United States Patent
Traverso et al.

(10) Patent No.: US 11,278,432 B2
(45) Date of Patent: Mar. 22, 2022

(54) UNDERACTUATED PROSTHETIC HAND

(71) Applicants: FONDAZIONE ISTITUTO ITALIANO DI TECNOLOGIA, Genoa (IT); INAIL-ISTITUTO NAZIONALE PER L'ASSICURAZIONE CONTRO GLI INFORTUNI, Rome (IT)

(72) Inventors: Simone Traverso, Genoa (IT); Andrea Lince, Fresonara (IT); Matteo Laffranchi, Genoa (IT); Lorenzo De Michieli, Genoa (IT); Nicolò Boccardo, Genoa (IT)

(73) Assignees: FONDAZIONE ISTITUTO ITALIANO DI TECNOLOGIA, Genoa (IT); INAIL-ISTITUTO NAZIONALE PER L'ASSICURAZIONE CONTRO GLI INFORTUNI, Rome (IT)

(*) Notice: Subject to any disclaimer, the term of this patent is extended or adjusted under 35 U.S.C. 154(b) by 0 days.

(21) Appl. No.: 17/053,503

(22) PCT Filed: May 6, 2019

(86) PCT No.: PCT/IB2019/053682
§ 371 (c)(1),
(2) Date: Nov. 6, 2020

(87) PCT Pub. No.: WO2019/215577
PCT Pub. Date: Nov. 14, 2019

(65) Prior Publication Data
US 2021/0128323 A1  May 6, 2021

(30) Foreign Application Priority Data

May 9, 2018  (IT) .................. 102018000005213

(51) Int. Cl.
A61F 2/58 (2006.01)
A61F 2/72 (2006.01)
(Continued)

(52) U.S. Cl.
CPC .............. A61F 2/586 (2013.01); A61F 2/583 (2013.01); A61F 2/72 (2013.01);
(Continued)

(58) Field of Classification Search
CPC ............. A61F 2/54; A61F 2/586; A61F 2/583
See application file for complete search history.

(56) References Cited

U.S. PATENT DOCUMENTS

2004/0054424 A1* 3/2004 Matsuda .............. B25J 15/0009
623/64
2006/0129248 A1* 6/2006 Stark ........................ A61F 2/70
623/63
(Continued)

FOREIGN PATENT DOCUMENTS

| GB | 2537898 A | 11/2016 |
|----|-----------|---------|
| WO | 2017077429 A1 | 5/2017 |
| WO | 2017199127 A1 | 11/2017 |

OTHER PUBLICATIONS

The International Search Report and Written Opinion, dated Aug. 27, 2019.

*Primary Examiner* — Bruce E Snow
(74) *Attorney, Agent, or Firm* — Vorys, Sater, Seymnour and Pease LLP

(57) ABSTRACT

Underactuated prosthetic hand including base body; first and second prosthetic fingers each hinged to the base body; first control cable; actuator to move the first control cable; and for each pair of fingers second control cable having control ends associated with the first and second fingers; and transmission block to allow first control cable to control second control cable; transmission block includes guide integral
(Continued)

with base body and defining sliding axis; movable element sliding along guide; first pulley for sliding first control cable hinged to movable element and second pulley for sliding second control cable hinged to the movable element so actuator, when moving first cable, determines moveable element translational movement to displace second control cable and the fingers; and elastic means opposing moveable element translational movement so the moveable element translational movement opposes elastic means allowing them to facilitate return to moveable element initial position.

11 Claims, 11 Drawing Sheets

(51) Int. Cl.
*A61F 2/50* (2006.01)
*A61F 2/68* (2006.01)

(52) U.S. Cl.
CPC .......... *A61F 2002/5038* (2013.01); *A61F 2002/5043* (2013.01); *A61F 2002/5072* (2013.01); *A61F 2002/5093* (2013.01); *A61F 2002/587* (2013.01); *A61F 2002/6854* (2013.01)

(56) References Cited

U.S. PATENT DOCUMENTS

| | | | |
|---|---|---|---|
| 2015/0297367 A1* | 10/2015 | Baba | A61F 2/70 623/64 |
| 2016/0089251 A1 | 3/2016 | Mandl et al. | |
| 2016/0166409 A1* | 6/2016 | Goldfarb | A61F 2/72 623/25 |
| 2017/0049583 A1 | 2/2017 | Belter et al. | |
| 2021/0228383 A1* | 7/2021 | Traverso | A61F 2/68 |

* cited by examiner

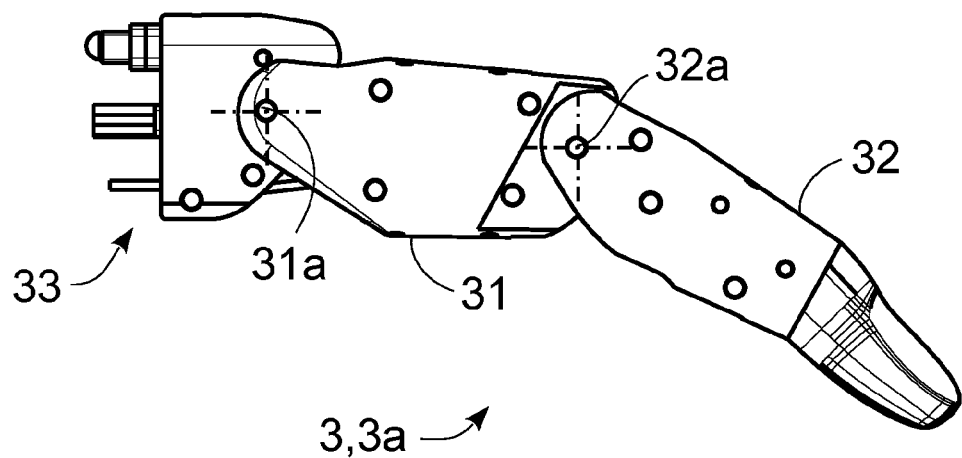
*Fig. 8a*
*Fig. 8b*
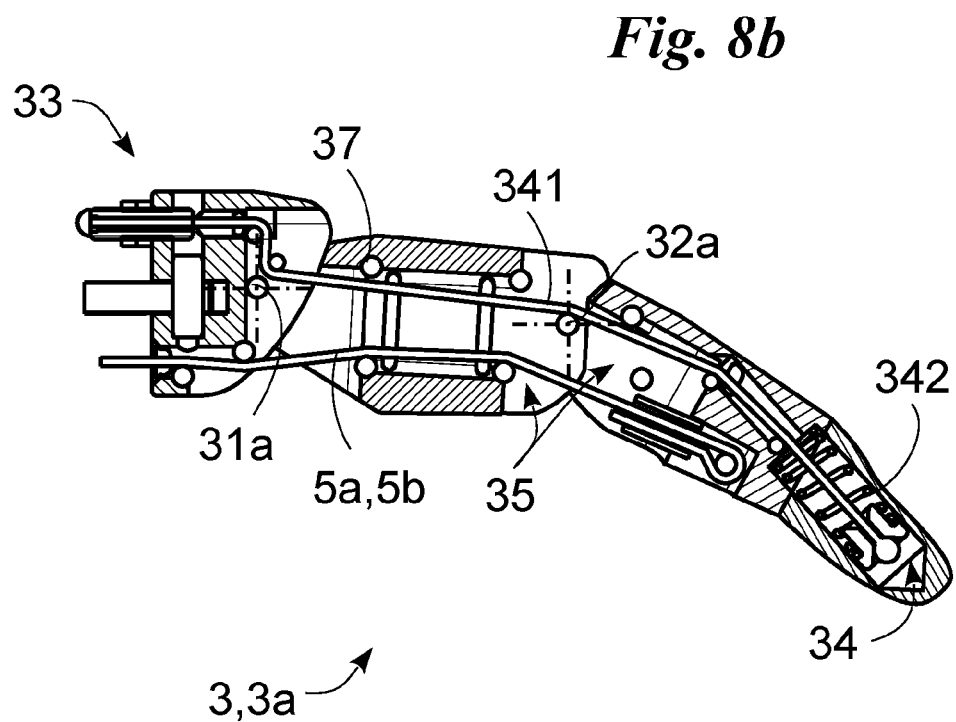

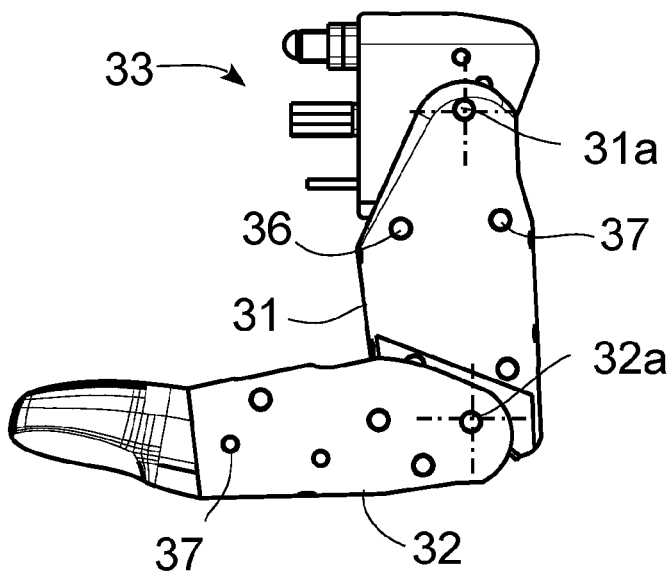
*Fig. 10a*
*Fig 10b*
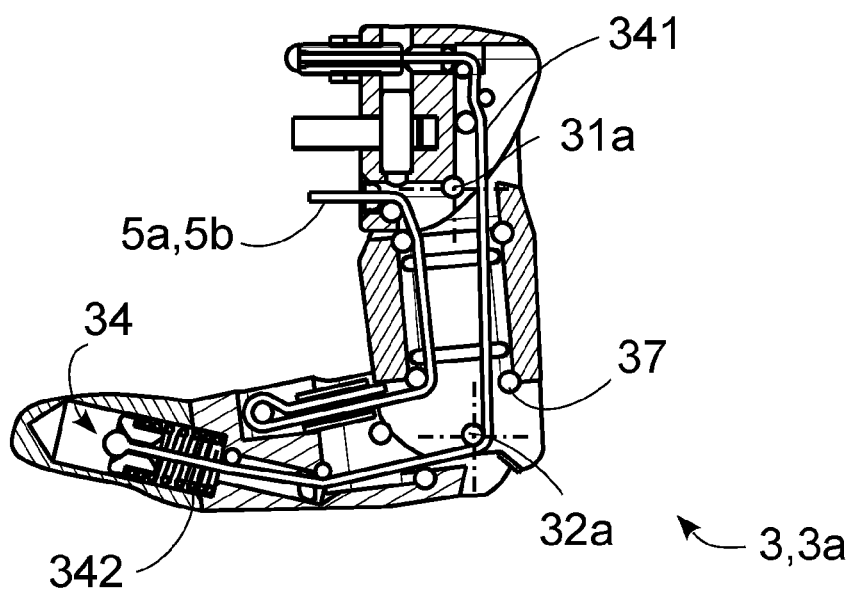

UNDERACTUATED PROSTHETIC HAND

The present invention relates to an underactuated prosthetic hand of the type as recited in the preamble of the first claim.

In particular, the object of the present invention is a robotic hand and, in particular, a prosthetic or myoelectric hand having fewer actuators than the degrees of freedom and capable of reproducing the movements of a human hand.

Prosthetic hands are used to replace a body segment in order to restore bodily integrity with particular attention to aesthetics.

These hands consist of an anchor body to the prosthetic limb or arm, a body articulated to it by a wrist rotatable with respect to the anchor body, and one or more fingers hinged to the main body. Each finger consists of a series of reciprocally hinged phalanges.

Prosthetic hands may include an electric actuator for moving each of the degrees of freedom of the hand and an actuator control unit.

This type of prosthetic hand is extremely complex and cumbersome and therefore underactuated hands have been designed with fewer actuators than the degrees of freedom of the hand.

Examples of undeactuated prosthetic hands are WO2017077429 and WO2017199127.

The prior art described has several significant drawbacks.

A first drawback is represented by the dimensions of both prosthetic fingers and hands, which are still very relevant today. It should be noted that this drawback is evident in the fingers where the actuation kinematics used to date are complex and cumbersome.

This drawback is significant in prosthetic hands where the large dimensions and weight compromise usability.

Another drawback of the known prosthetic hands lies in the unnatural nature of the movements and therefore the practical impossibility of gripping objects naturally regardless of the shape and size of the object. This aspect is extremely evident in the case of small objects which it is almost impossible to grip precisely and safely. A no less important drawback is the fact that the prosthetic hands known to date have a human-machine interface that is not easy to learn.

In this situation the technical purpose of the present invention is to devise an underactuated prosthetic hand able to substantially overcome at least some of the drawbacks mentioned.

Within the sphere of said technical purpose one important aim of the invention is to obtain an underactuated prosthetic hand of smaller dimensions, weight and therefore easily applicable and utilisable as a prosthesis.

Another important object of the invention is to make an underactuated prosthetic hand having natural movements and grips especially of small objects.

A further purpose is to have an underactuated prosthetic hand with a simple man-machine interface.

The technical purpose and specified aims are achieved by an underactuated prosthetic hand as claimed in the appended claim 1. Examples of preferred embodiment are described in the dependent claims.

The characteristics and advantages of the invention are clearly evident from the following detailed description of preferred embodiments thereof, with reference to the accompanying drawings, in which:

FIG. 8a shows, in scale, a prosthetic finger of the prosthetic hand according to the invention;

FIG. 8b shows, in scale, a cross-section of FIG. 8a;

FIG. 9b shows, in scale, a cross-section of FIG. 9a;

Figure 11A:
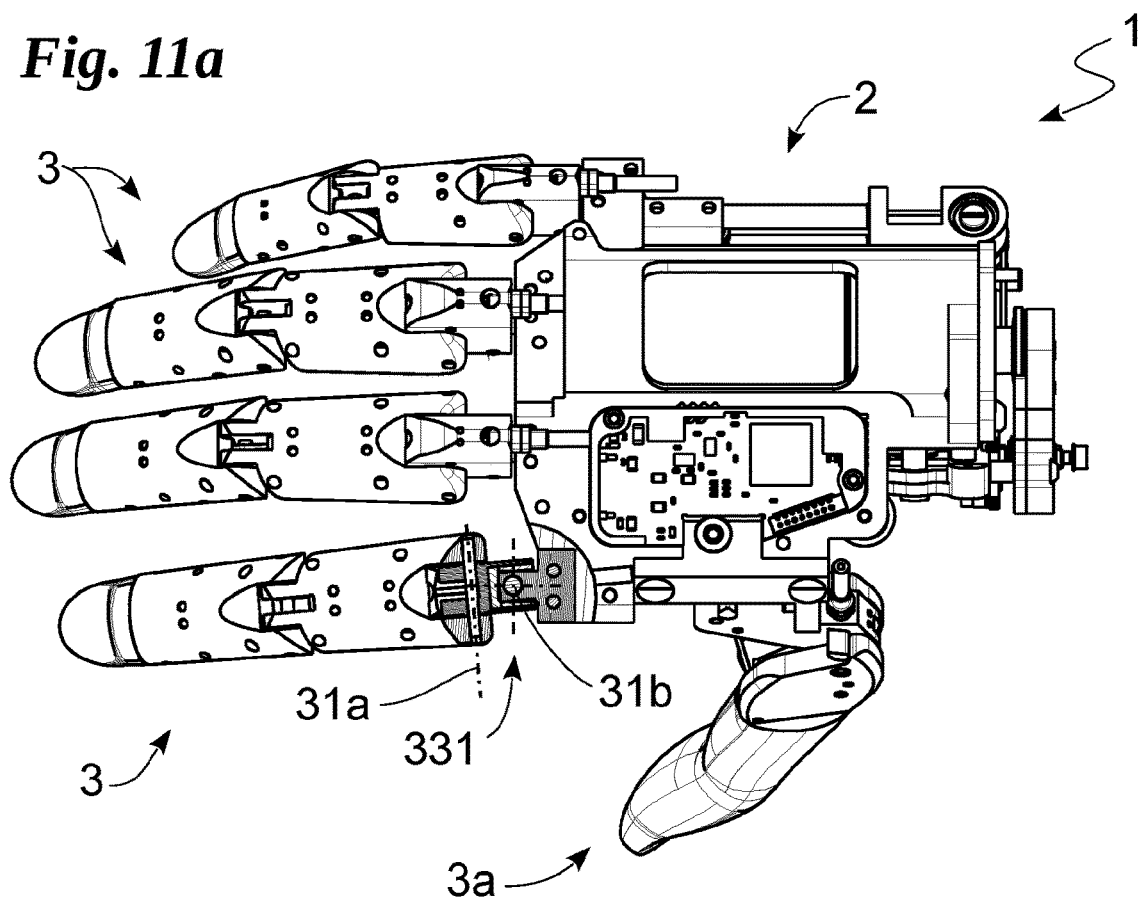
Figure 11B:
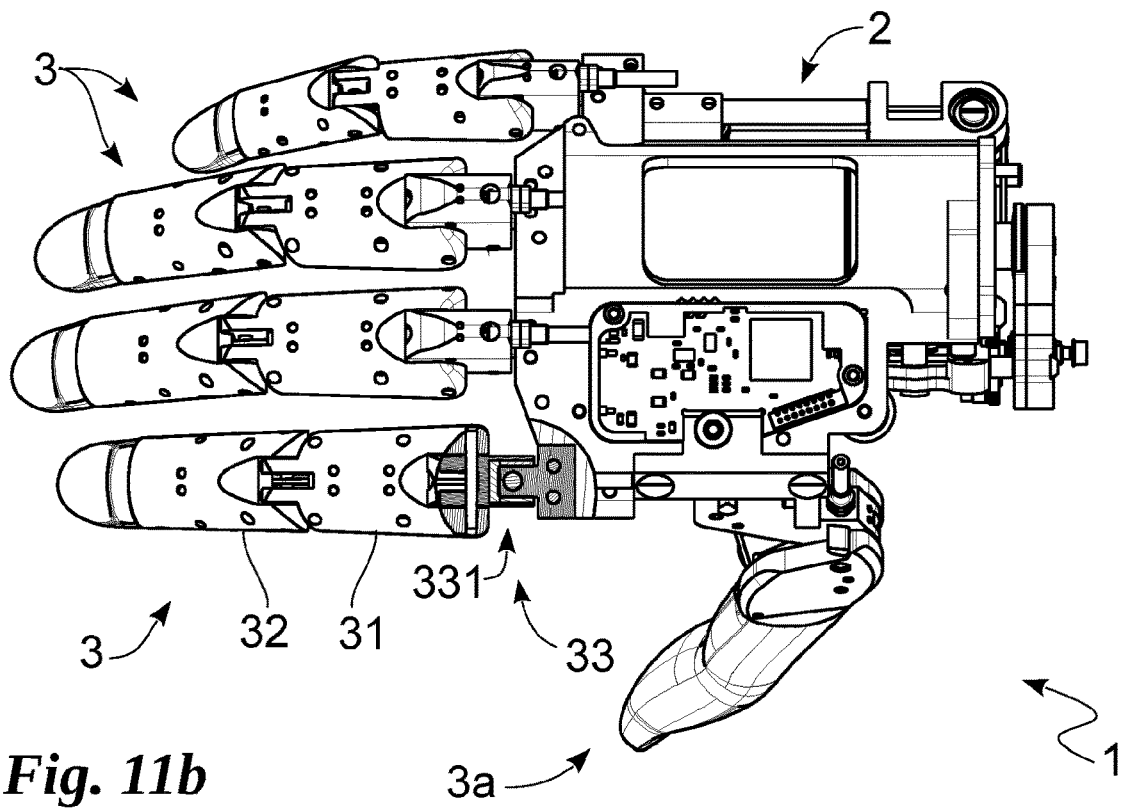
Figure 12A:
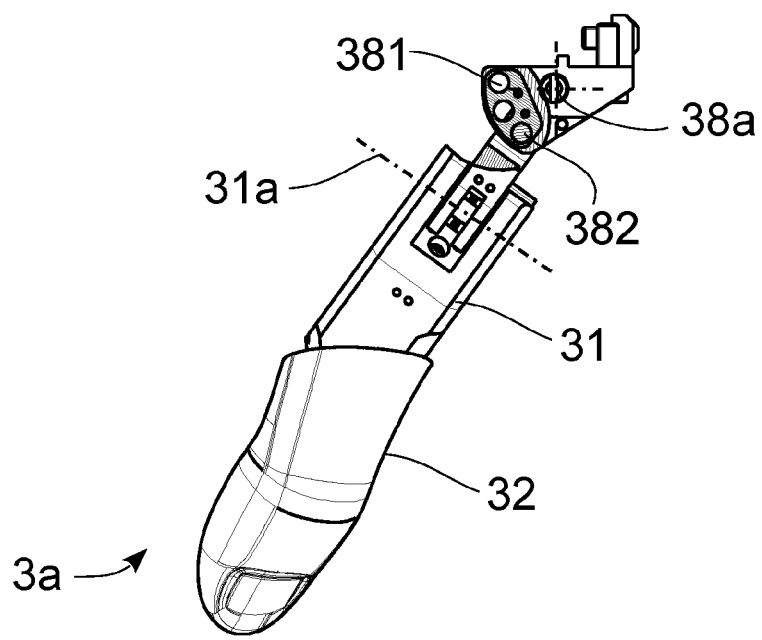
Figure 12B:
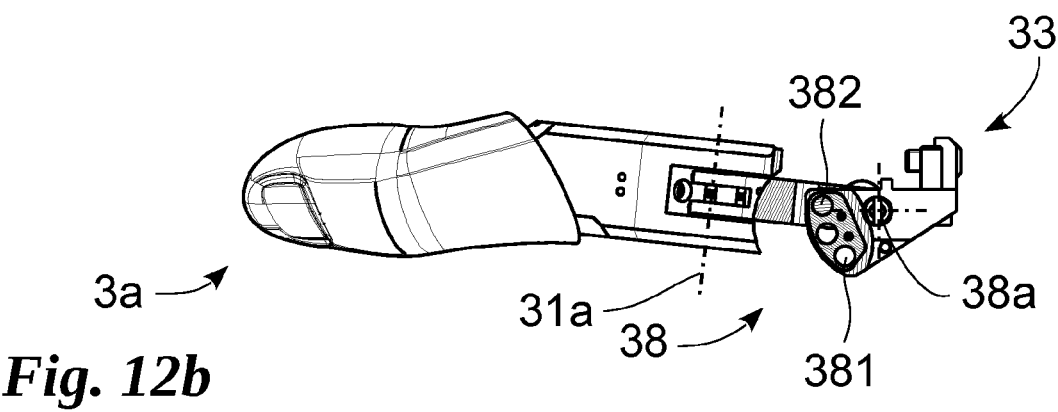

FIG. 10a proposes, in scale, the component of FIG. 8a in a further pose;

FIG. 10b is, in scale, a cross-section of FIG. 10a;

FIG. 11a shows, in scale, a detail of the underactuated prosthetic hand according to the invention;

FIG. 11b shows, in scale, the hand of FIG. 11a in a different position;

FIG. 12a shows, in scale, a component according to the invention;

FIG. 12b proposes, in scale, the component of FIG. 12a in another pose; and

Figure 12C:
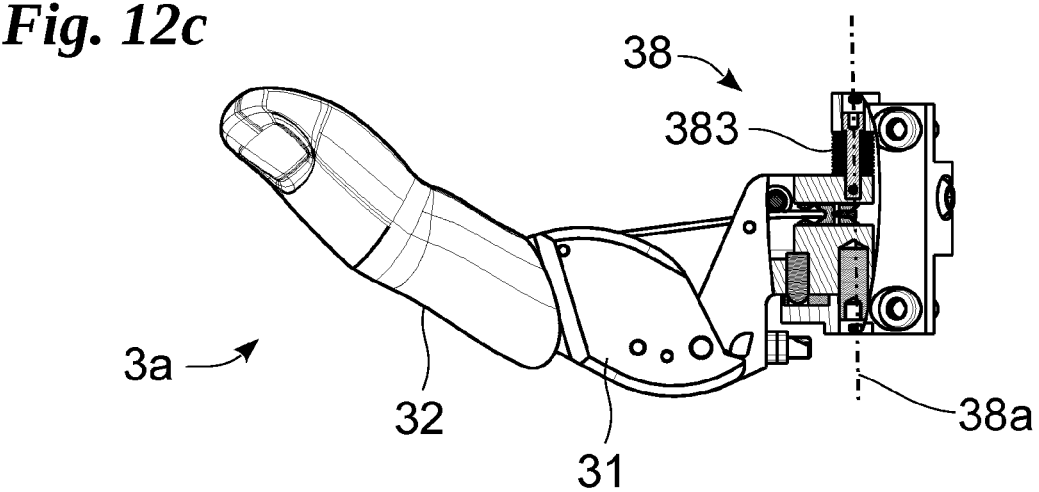

FIG. 12c is, in scale, a cross-section of the component of FIGS. 12a and 12b.

Herein, the measures, values, shapes and geometric references (such as perpendicularity and parallelism), when used with words like "about" or other similar terms such as "approximately" or "substantially", are to be understood as except for measurement errors or inaccuracies due to production and/or manufacturing errors and, above all, except for a slight divergence from the value, measure, shape or geometric reference which it is associated with. For example, said terms, if associated with a value, preferably indicate a divergence of not more than 10% of said value.

In addition, where used terms such as "first", "second", "upper", "lower", "main" and "secondary" do not necessarily refer to an order, a priority relationship or relative position, but may simply be used to more clearly distinguish different components from each other.

The measurements and data presented herein are to be considered, unless otherwise indicated, as made in Standard International Atmospheres ICAO (ISO 2534).

Except where specified otherwise, as evidenced by the discussions below, it should be noted that terms such as "processing", "computer", "computing", "evaluation", or the like, refer to the action and/or a processes of a computer or similar electronic calculation device, which handles and/or processes data represented as physical, electronic, sizes of logs of computer system and/or memories in other data similarly represented as physical quantities inside computer systems, logs or other information storage, transmission or display devices.

With reference to the Drawings, reference numeral 1 globally denotes the underactuated prosthetic hand according to the invention.

It comprises a base body 2; and at least one finger and in detail several fingers hinged to the base body 2.

The base body 2 is suitable to be constrained to an external element such as a robotic arm or a human limb.

The base body 2 defines a main extension surface.

The base body 2 identifies the palm of the underactuated prosthetic hand 1.

In detail, the underactuated prosthetic hand 1 comprises at least one prosthetic finger 3 hinged to the base body 2 and precisely at least a pair of prosthetic fingers 3 each of which, suitably individually, hinged to the base body 2. Preferably it comprises two pairs of prosthetic fingers 3. More preferably the prosthetic hand comprises a first pair of fingers identifying index finger and middle finger and a second pair identifying ring finger and small finger.

Each pair comprising a first prosthetic finger 3 (e.g. index finger or ring finger) and a second prosthetic finger 3 (e.g. middle finger or small finger).

In addition to said prosthetic fingers 3 the underactuated prosthetic hand 1 may comprise an additional finger 3a (FIGS. 12a-12c)

The additional finger 3a is suitable to work in opposition to one or more prosthetic finger(s) 3 to generate the gripping of the objects.

The additional finger 3a is identifiable in the thumb.

Each prosthetic finger 3 and/or 3a (i.e. each prosthetic finger 3 and/or additional finger 3a), as shown in FIGS. 8a-10b, comprises a phalanx 31 proximal to the base body 2 and a phalanx 32 distal from the base body.

The proximal phalanx 31 is hinged to the base body 2 defining a first rotation axis 31a. Specifically, each prosthetic finger 3 and/or 3a may comprise an attachment 33 suitable to connect the prosthetic finger 3 and in particular the proximal phalanx 31 to an external body; and the proximal phalanx 31 is hinged to the attachment 33 and thus to the base body 2.

The first axis 31a may be substantially parallel to the main extension surface of the base body 2.

The attachment 33 is suitable to be connected to the base body 2.

The distal phalanx 32 is hinged to the proximal phalanx 31 opposite the base body 2 defining a second rotation axis 32a.

Suitably the first rotation axis 31a is substantially parallel to the main extension surface of the base body 2.

Preferably the axes 31a and 32a of a prosthetic finger 3 and/or 3a are substantially parallel to each other.

Optionally, a prosthetic finger 3 and/or 3a may comprise an intermediate phalanx hinged between the proximal phalanx 31 and distal phalanx 32.

Preferably the distal phalanx 32 and the proximal phalanx 31 of the additional finger 3a are integral with each other and therefore the additional finger 3a is devoid of a second axis 32a.

The additional finger 3a may comprise an approach mechanism 38 defining an approach axis 38a around which the additional finger 3a rotates approaching or moving away from the base body 2.

The approach mechanism 38 is suitable to block the rotation of the additional finger 3a about the approach axis 38a with respect to the base body 2 and/or the attachment 33.

Optionally all the fingers 3 and 3a comprise an approach mechanism 38.

The approach mechanism 38 defines, with respect to the approach axis 38a, at least one angular locking position and specifically a first rotational locking position (FIG. 12a) of the additional finger 3a with respect to the base body 2 and a second rotational locking position (FIG. 12b) of the additional finger 3a with respect to the base body 2. The angular variation between the first and second angular locking positions, calculated with respect to a plane parallel to the plane of the base body 2 and a plane passing through the additional finger 3a and perpendicular to the axis 31a of the additional finger 3a with respect to the body 2, may be substantially between 45° and 75° and, specifically, substantially equal to 60°.

Preferably, the approach mechanism 38 defines an intermediate rotational locking position suitably interposed and equidistant from the first and second rotational locking positions.

The approach mechanism 38 (FIG. 12c) comprises a cavity 381 for each rotational locking position made in the base body 2 and/or the attachment 33; a stop 382 associated with the additional finger 3a and suitable to fit into a cavity 381 defining a rotational locking position.

The approach mechanism 38 may comprise return means 383 of the finger 3a suitable to push, suitably along the axis 38a, and keep the stop 382 in a suitably elastic cavity 381.

The approach mechanism 38 may comprise an elastic component suitable to control the insertion of the stop 382 into the cavities 381 and thus to work in opposition to the exit of the stop from a cavity 381.

The one or more cavities 381 are formed on the base body 2 and/or on the attachment 33.

During a rotation of the additional finger 3a the stop comes out of a cavity compressing the elastic component. When the stop faces a cavity the elastic component pushes the stop into the cavity and thus blocks the rotation of the additional finger 3a thereby realizing each rotational locking position.

Finally, the locking mechanism may comprise one or more stopping members suitable to limit the rotation of the additional finger 3a between the first and second rotational locking positions.

In some cases at least one prosthetic finger 3 and, specifically, all the fingers 3 are hinged to the base body defining, in addition to the first rotation axis 31a, an additional first rotation axis 31b (FIGS. 11a and 11b). Said additional first rotation axis 31b is substantially perpendicular to the main extension surface of the base body 2.

The additional first rotation axis 31b is interposed between the base body 2 and the first rotation axis 31a.

An attachment 33 may comprise a hinge 331 defining said additional first rotation axis 31b.

The rotation around the additional first rotation axis is passive (i.e. not controlled by a motor\actuator) and therefore can only be controlled by agents external to the hand 1. Consequently, the hinge 331 comprises one or more elastic deformation elements suitable to deform elastically in opposition to a rotation of the prosthetic finger 3 around the additional first rotation axis. Specifically, the hinge 331 comprises a first elastic deformation element and a second elastic deformation element each suitable to deform elastically in opposition to a rotation of the prosthetic finger 3 around the additional first rotation axis in a direction of rotation. Preferably the range of rotation about the additional first rotation axis 31b is substantially between 5° and 20°.

The underactuated prosthetic hand 1 comprises at least one actuator 4 suitable to control a rotation of one or more fingers 3 and/or 3a. In detail, the underactuated prosthetic hand 1 is mono-actuated and comprises only one actuator 4.

The actuator 4 is suitable to control the rotation of the phalanges 31 and 32 and, specifically, the proximal phalanx 31 with respect to the base body 2 around the first rotation axis 31a and the distal phalanx 32 with respect to the proximal phalanx 31 around the second rotation axis 32a.

The actuator 4 is upstream of the fingers 3 and/or 3a along the kinematic chain of the underactuated prosthetic hand 1. In detail, it can be attached to the base body 2.

The actuator 4 is preferably electric.

The underactuated prosthetic hand 1 comprises at least one control cable by means of which the actuator 4 moves the fingers 3 and/or 3a in a first direction.

Figure 7:
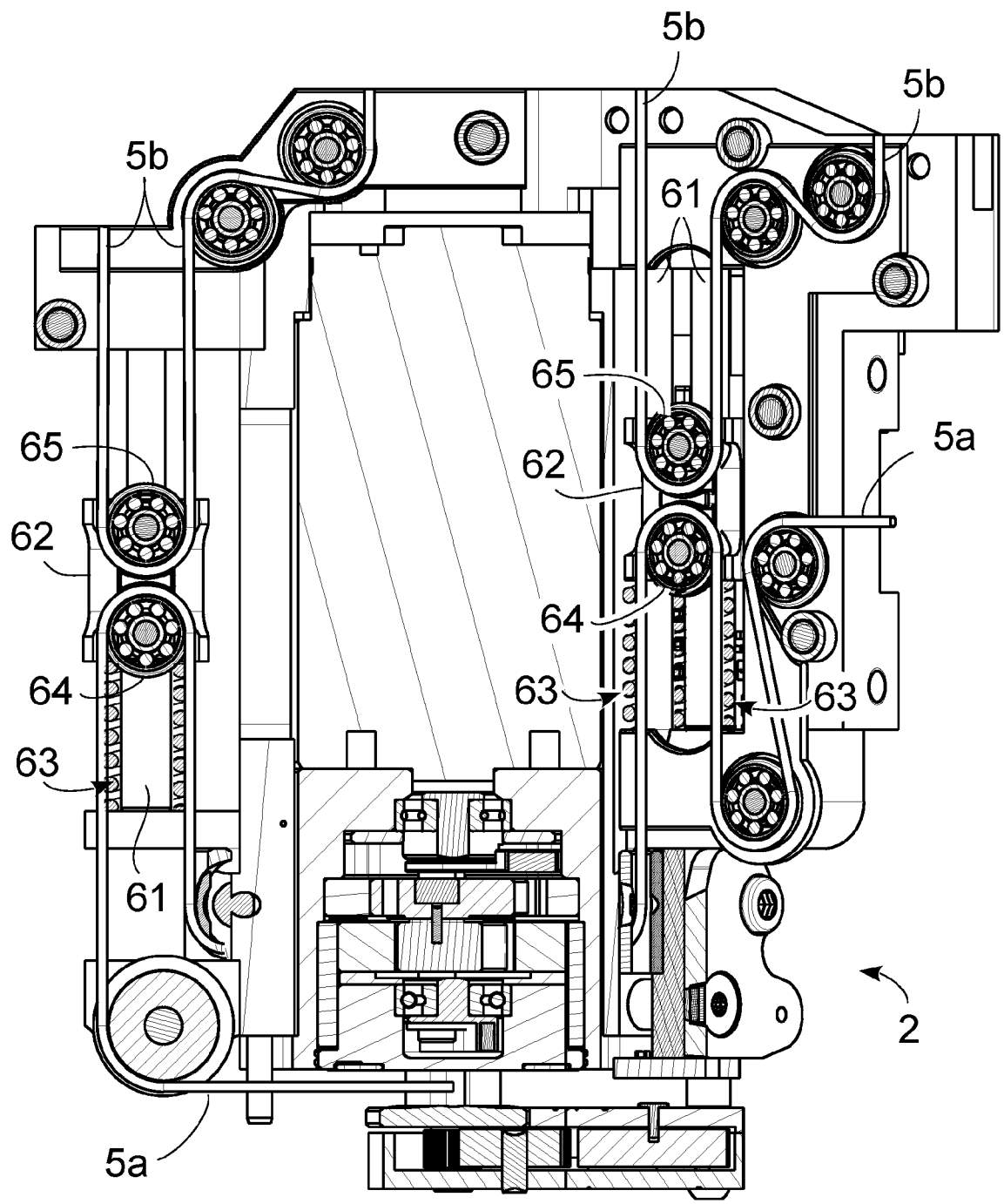
FIG. 7 illustrates, in scale, an assembly of the underactuated prosthetic hand in the central body part only.
Figure 9A:
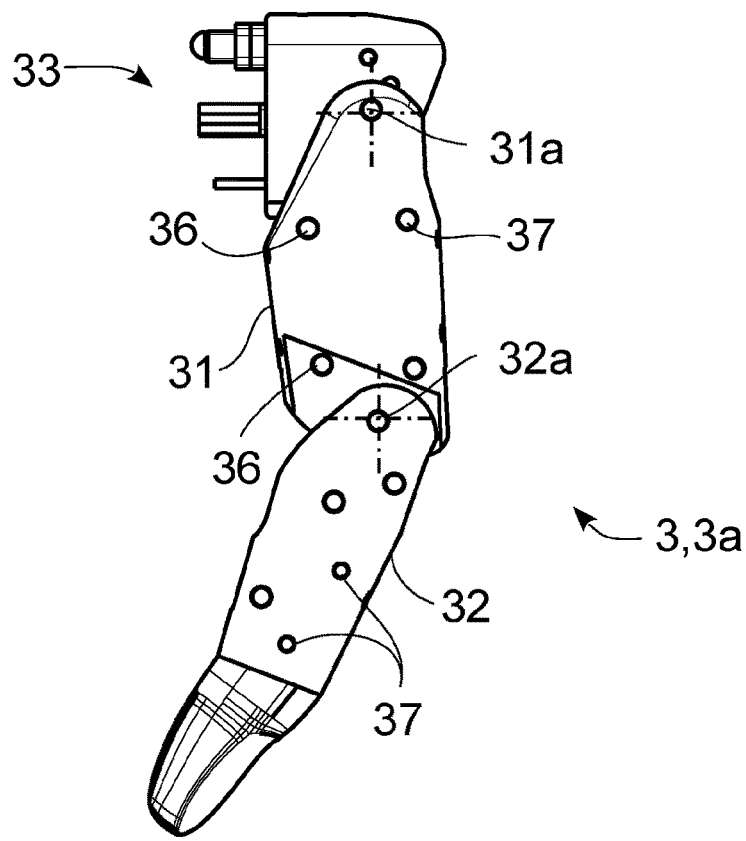
FIG. 9a shows, in scale, the component of FIG. 8a in a different pose.
Figure 9B:
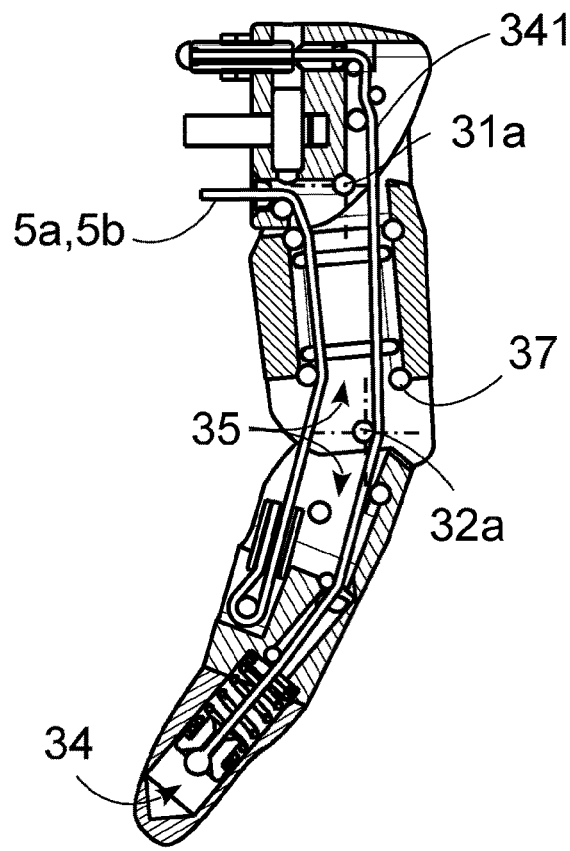

In detail, the underactuated prosthetic hand 1 comprises a first control cable 5a suitable to be moved by the actuator 4; at least one second control cable 5b; and at least one transmission block 6 suitable to allow the first control cable 5a to control the second control cable 5b. Preferably it comprises two pairs of prosthetic fingers 3, a single first cable 5a, two second cables 5b and two blocks 6 by means of which the first control cable 5a and thus the actuator 4 control, suitably simultaneously, both second cables 5b (FIG. 7).

The control cables 5a and/or 5b may be made of polyethylene fibre.

The first control cable 5a defines a first control end integral with the base body and suitably a second control end integral with the actuator 4. In the case of a prosthetic hand 1 comprising the additional finger 3a, the first cable 5a is suitable to control said additional finger 3a and the first control end of the first control cable 5a is integral with the additional finger 3a and, specifically, with the distal phalanx 32 of the additional finger 3a.

The second control cable 5b has a first control end constrained to a first prosthetic finger 3 of a pair of prosthetic fingers 3 and a second control end constrained to the second prosthetic finger 3 of said pair of prosthetic fingers 3. Preferably it has the first control end associated with the distal phalanx 32 of the first prosthetic finger 3 and the second control end associated with the distal phalanx 32 of the second prosthetic finger 3.

Figure 5:
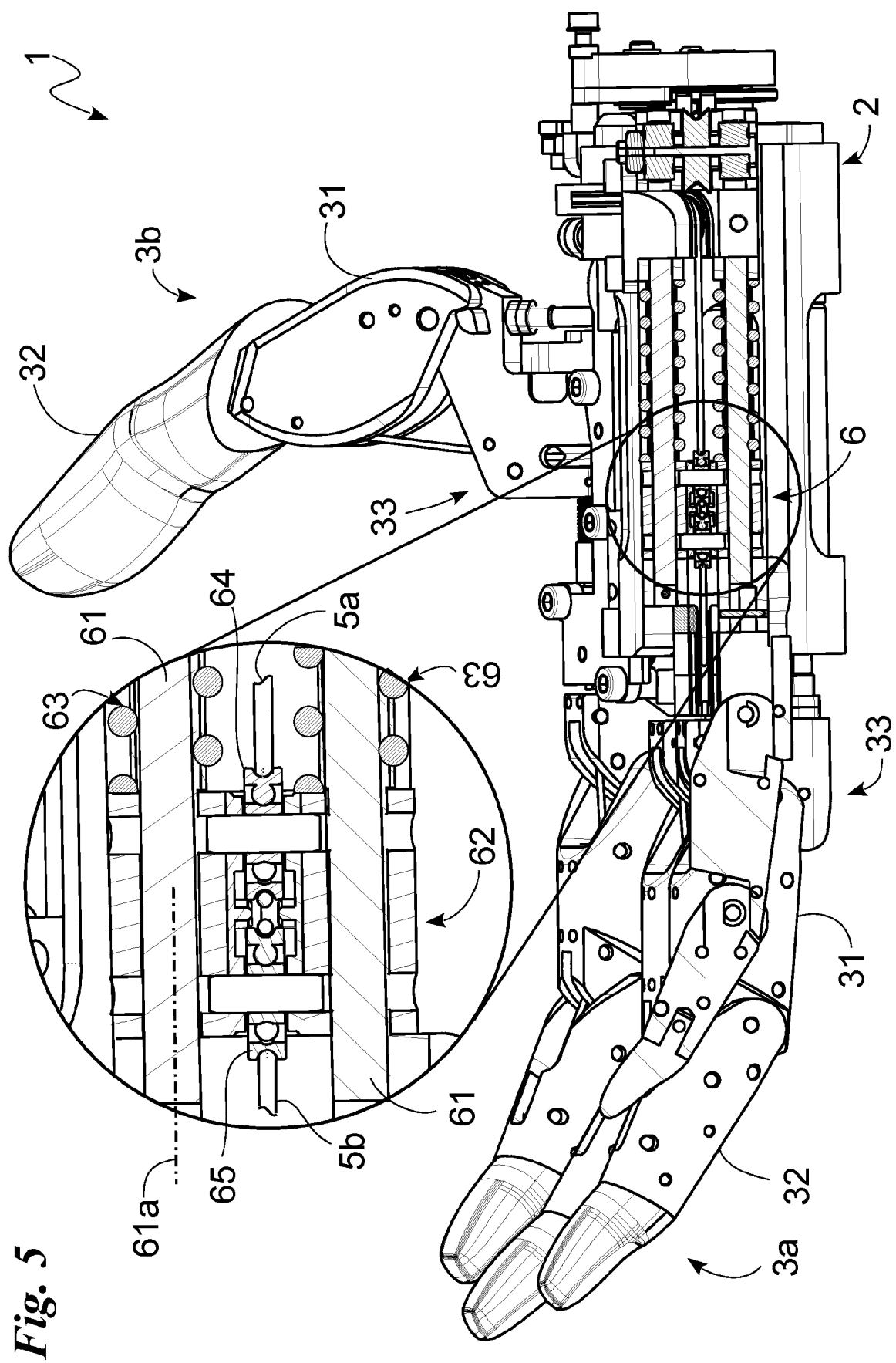
FIG. 5 shows, in scale, a second cross-section of FIG. 1.
Figure 6:
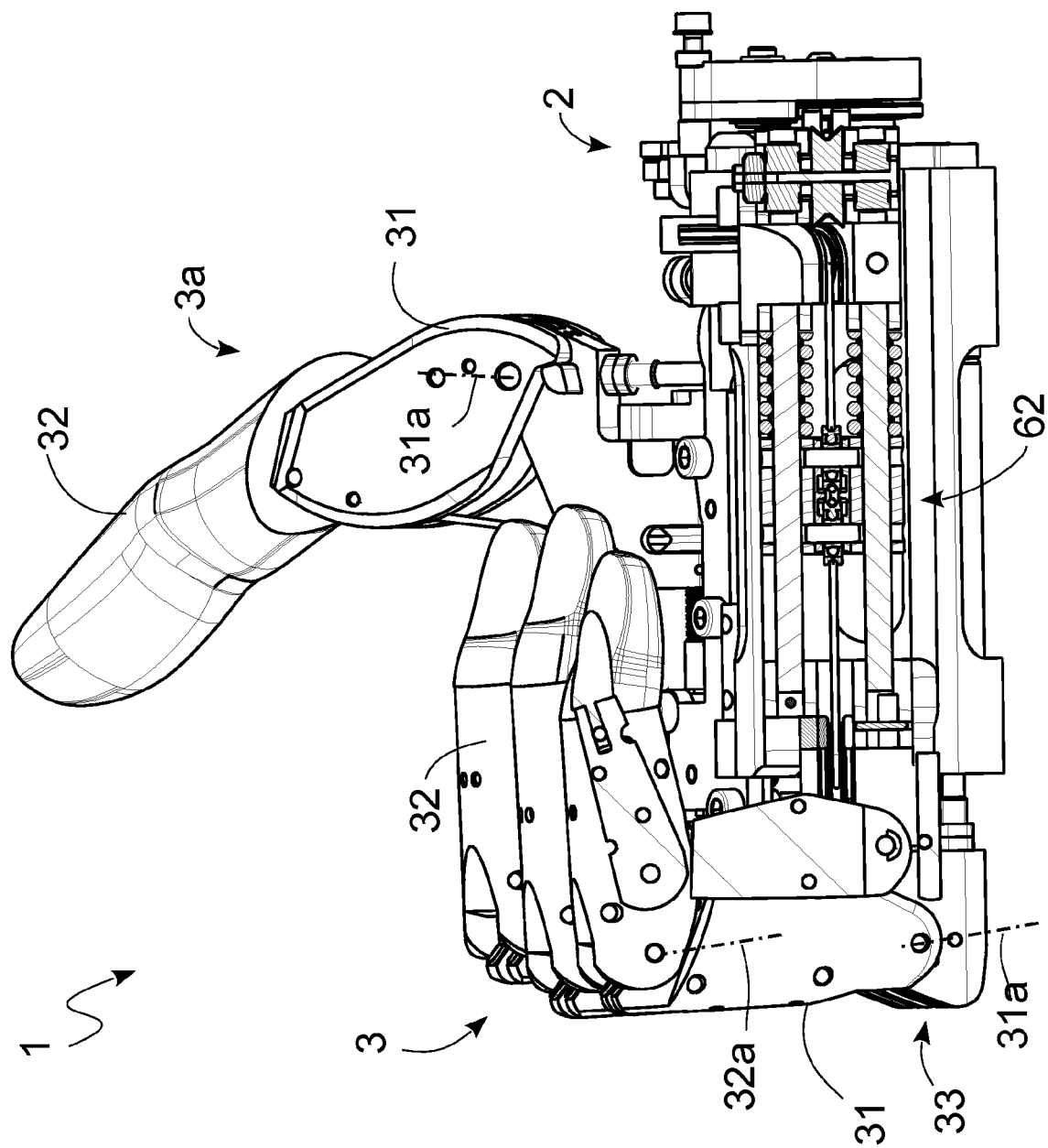
FIG. 6 is, in scale, a second cross-section of FIG. 2.

The transmission block 6 (see FIG. 5) comprises at least one guide 61 integral with the base body 2; a movable element 62 sliding along the guide 61; elastic means 63 suitable to oppose a sliding of the movable element 62 along the guide 61; a first pulley 64 for the sliding of the first control cable 5a hinged to the movable element 62; and a second pulley 65 for the sliding of the second control cable 5b hinged to the movable element 62 so that the actuator 4, when moving the first control cable 5a, determines a translational movement of the movable element 62 along the guide 61.

Preferably, the transmission block 6 comprises two guides 61 parallel to each other and the movable element 62 slides along the guides 61.

The guides 61 of the two blocks 6 are substantially parallel to each other.

The translational movement of the movable element 62, the pulleys 64 and 65 being hinged thereto, causes a displacement of the second control cable 5b thus moving the prosthetic fingers 3. Specifically, the translational movement of the movable element 62 results in a rotation, suitably equivalent, of the phalanges 31 and 32 about the axes 31a and 32a in a first direction. It is to be noted that at the same time a rotation can occur with respect to the base body 2 of the additional finger 3a in a first direction generating the grip.

In this document the term "first direction" identifies a rotation controlled by the actuator 4 while the "second direction" identifies a rotation opposite to that of the first direction.

The translational movement of the movable element 62 is carried out in opposition to the elastic means 63 which, upon deactivation of the actuator 4 (i.e., when it does not exert torque/force on the first cable 5a), commands the return to the initial position of the movable element 62. In detail, the action of the means 63 facilitates a rotation of the prosthetic fingers 3 suitably equivalent, of the phalanges 31 and 32 in a second direction opposite the first and bringing the prosthetic fingers 3 back to the initial position. At the same time, the return to the initial position of the movable elements 62 causes a rotation of the additional finger 3a in a second direction opposite the first.

The guide 61 is linear and defines a sliding axis 61a for the movable element 62. The two guides 61 have sliding axes 6a substantially parallel to each other.

The pulleys 64 and 65 define relative to the movable element 62 rotation axes nearly parallel to each other and substantially perpendicular to the sliding axis 61a. Alternatively said rotation axes may be inclined in relation to each other.

The elastic means 63 are suitable to keep the cable 5a taut. They are preferably preloaded.

The elastic means 63 comprise at least one coil spring coaxial to the sliding axis 61a. Specifically, they comprise, for each guide, a coil spring wrapped around the guide 61.

Said coil spring is a traction and preferably a compression spring.

Each prosthetic finger 3 and/or 3a comprises a return block 34 (FIGS. 8b-10b) suitable to work in opposition to a rotation of said finger and in particular of the phalanges 31 and 32 controlled by the actuator 4 and therefore by a control cable 5a and/or 5b.

The return block 34 is suitable to rotate the phalanges 31 and 32 in the second direction. It should be noted that such motion is preferably controlled by the block 34 alone while the elastic means 63 facilitate such motion by loosening the control cable 5b.

The return block 34 comprises a return cable 341 defining a first return end connected to the base body 2 and a second return end connected to the distal phalanx 32; and an elastic body 342 suitable to keep said secondary cable taut. The return cable 341 has the first return end integral with the base body 2 and preferably with the attachment 33. Such attachment 33, being constrained to the base body 2, allows the first end of the return cable 341 to be integral with the base body 2.

The return cable 341 has the second return end integral with the elastic body 342 thus interposed between said second end and distal phalanx 32.

The return cable 341 is opposite the control cable 5a and/or 5b with respect to the rotation axes 31a and 32a. Preferably, the return cables 341 of an underactuated prosthetic hand 1 are, with respect to all the rotation axes 31a and 32a of the underactuated prosthetic hand 1, opposite the control cables 5a and/or 5b so that the fingers 3 and/or 3a rotate in a parallel and concordant manner when actuated by both the return cables 341 and the control cables 5a and/or 5b.

The elastic body 342 is suitable to keep the return cable 341 in tension and to work in opposition to the control cable 5a and/or 5b. Consequently, when the actuator 4 is activated, the control cable 5a and/or 5b, rotating the phalanges 31 and 32 in the first direction, moves the return cable 341 loading the elastic body 342 which, upon deactivation of the actuator 4, can control a rotation of said phalanges 31 and 32 in the second direction.

The elastic body 342 is housed in the distal phalanx 32.

The elastic body 342 is a coil spring coaxial to the distal phalanx 32. Specifically, it is a traction spring and more specifically a compression spring.

The elastic body 342 may be preloaded so as to adjust the elastic response of the fingers 3 and/or 3a. Preferably the fingers 3 and/or 3a have different preloads of the elastic bodies 342 so as to differentiate the response\movement of said fingers. Each prosthetic finger 3 and/or 3a may comprise housing channels 35 for the cables 5a, 5b and/or 341 made in the phalanges 31 and 32. The cables 5a, 5b and/or 341 thus slide internally to the fingers 3 and/or 3a.

Each prosthetic finger 3 and/or 3a may comprise first sliding pins 36 for the control cable 5a and/or 5b; and second sliding pins 37 for the return cable 341.

The first pins 36 are positioned such that the control cable 5a and/or 5b defines a torque at the first rotation axis 31a greater than the torque at the second rotation axis 32a rotating the proximal phalanx 31 faster than the distal phalanx 32.

To such purpose, the distance between the control cable 5a and/or 5b and the first rotation axis 31a is greater than the distance between the control cable 5a and/or 5b and the second rotation axis 32a regardless of the angular position of the phalanges 31 and 32. Preferably the distance between the control cable 5a and/or 5b and the first rotation axis 31a is substantially between 200% and 100% and, specifically, between 125% and 200% and even more specifically between 125% and 175% of the distance between the control cable 5a and/or 5b and the second rotation axis 32a regardless of the angular position of the phalanges 31 and 32. For example, the distance between the control cable 5a and/or 5b and the first rotation axis 31a is substantially between 10 mm and 5 mm and, specifically, between 7 mm and 9 mm and even more specifically, between 7.32 mm and 8.88 mm. The distance between the control cable 5a and/or 5b and second rotation axis 32a is approximately 7 mm to 3 mm and, specifically, 4.5 mm to 6.5 mm and even more specifically, 5.35 mm to 5.89 mm.

Finally, each prosthetic finger 3 and/or 3a comprises at least one limit switch suitable to limit the rotation of a phalanx 31 and/or 32. Specifically, a prosthetic finger 3 and/or 3a comprises at least one first limit switch suitable to limit the rotation of the proximal phalanx 31 and at least one second limit switch suitable to limit the rotation of the distal phalanx 32. In more detail it comprises two first limit switches so as to limit rotation of the proximal phalanx 31 in both directions; and two second limit switches so as to limit rotation of the distal phalanx 32 in both directions.

Optionally a pin can have the function of limit switch.

The underactuated prosthetic hand 1 comprises a control unit suitable to control the underactuated prosthetic hand 1.

The control unit may be suitable to control the operation of the underactuated prosthetic hand 1 as a function of an electromyographic signal (variation of electrical potential during a contraction of a muscle). The underactuated prosthetic hand 1 may thus comprise at least one EMG sensor (or prosthetic or myoelectric sensor) suitable to measure a change in potential in a muscle and transmit to the control unit a signal proportional to such measurement.

The EMG sensor is per se known.

The functioning of the underactuated prosthetic hand described above in structural terms, is as follows.

Figure 1:
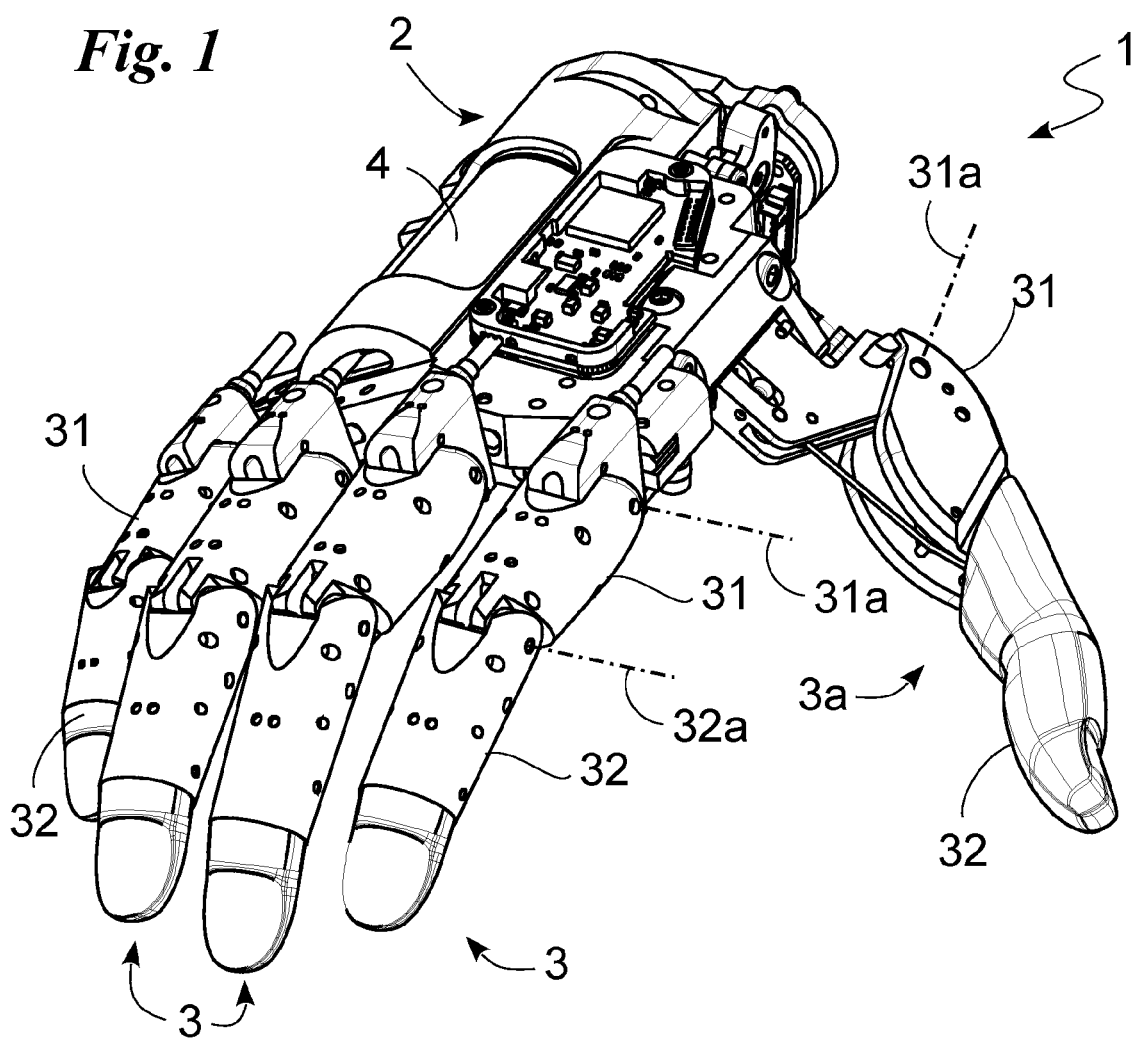
FIG. 1 shows, in scale, an underactuated prosthetic hand according to the invention.

Initially the underactuated prosthetic hand 1 is with the fingers 3 and/or 3a extended as shown in FIG. 1.

Figure 2:
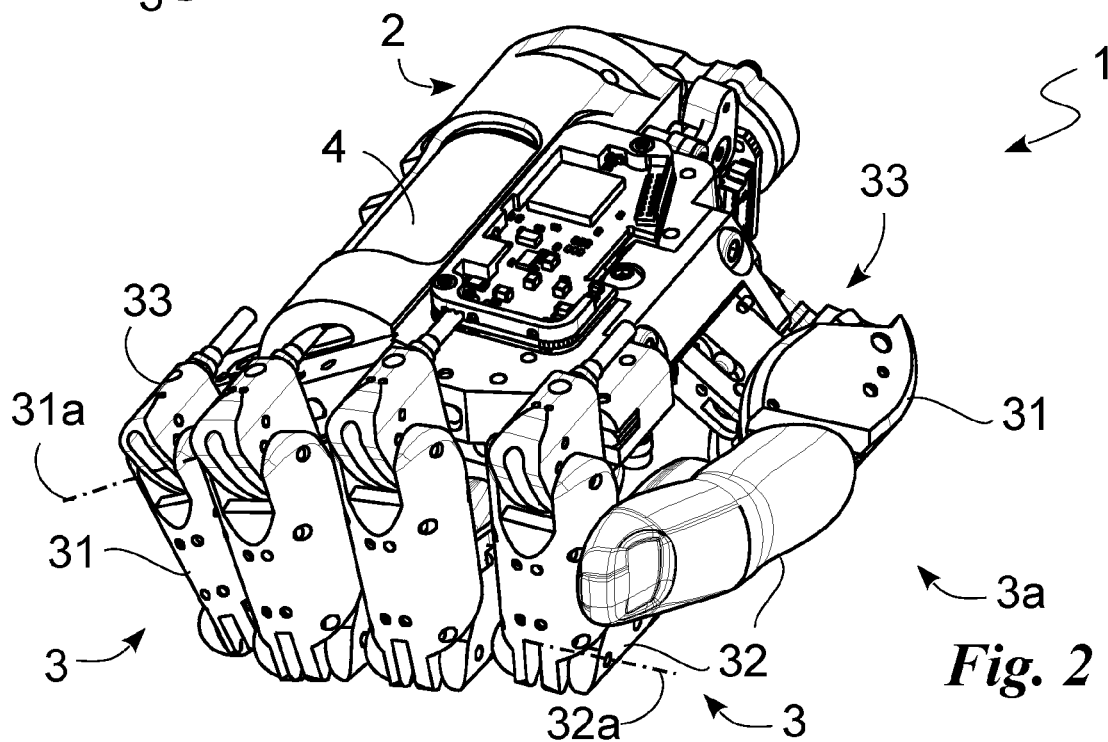
FIG. 2 illustrates, in scale, the hand in FIG. 1 in a different grip.
Figure 3:
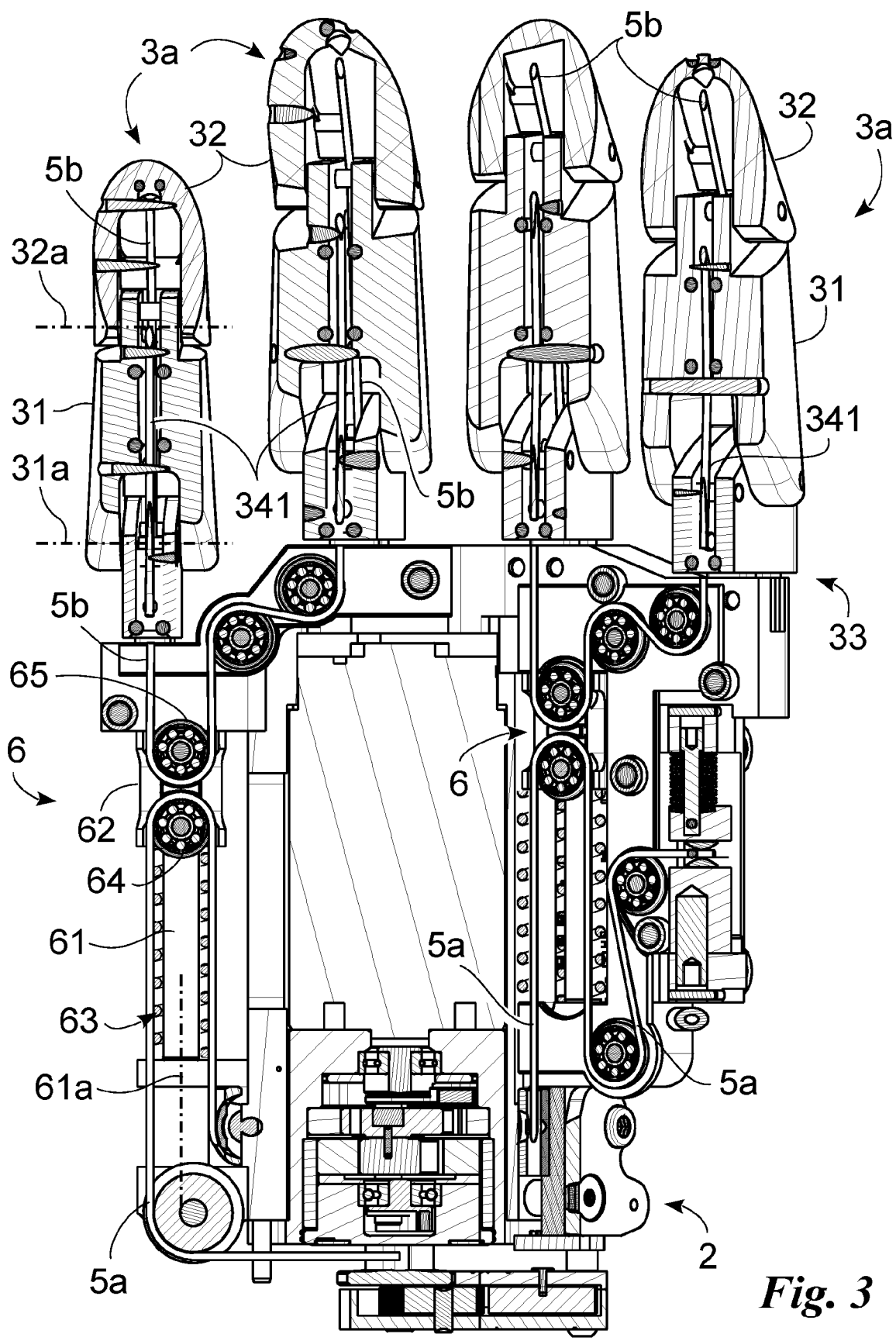
FIG. 3 shows, in scale, a cross-section of FIG. 1.
Figure 4:
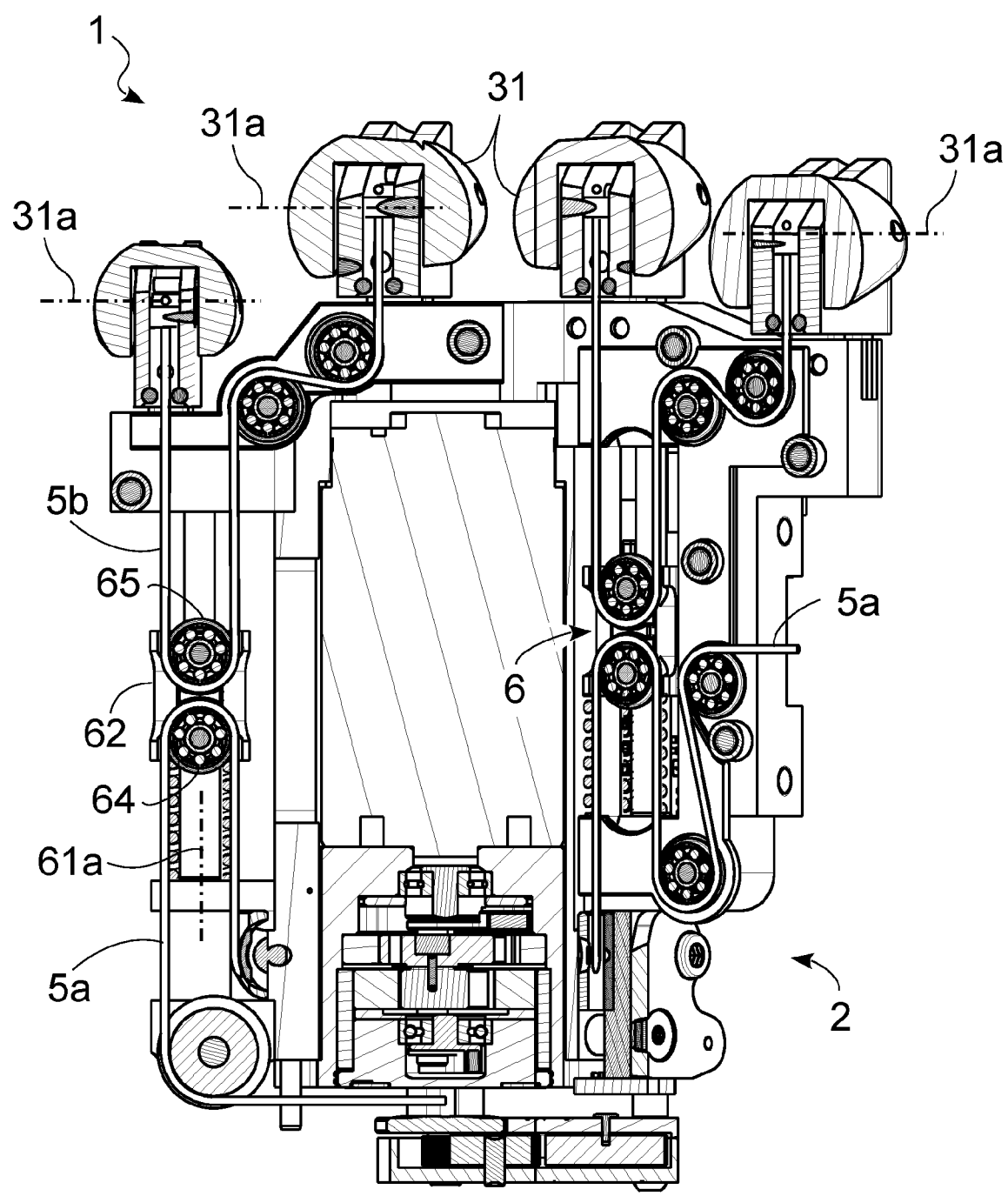
FIG. 4 is, in scale, a cross-section of FIG. 2.

When the user commands, for example by electromyographic signal, the transition into a gripping configuration (for example FIG. 2), the control unit activates the actuator 4.

The actuator 4 controls the first control cable 5a and through the two transmission blocks 6, the second control cables 5b. In detail, the first cable 5a controls, in opposition to the elastic means 63, the translational movement of the two movable elements 62 along the sliding axis 61a of the corresponding guide 61.

This translational movement of the movable element 62 moves the second control cable 5b which thus controls the rotation in a first direction of the phalanges 31 and 32 in opposition to the return cable 341.

If the underactuated prosthetic hand 1 envisages the additional finger 3a, the first control cable 5a, at the same time as the second cable 5b, moves said additional finger 3a and then rotates it in a first direction opposite the corresponding return cable 341.

In short, the actuator 4, taking advantage of the particular transition movement kinematics between the control cables 5a and 5b, simultaneously actuates the five fingers 3 and 3a of an underactuated prosthetic hand 1.

When the actuator ceases its action by relaxing the first control cable 5a the return cable 341 and the elastic means 63 command the return of the underactuated prosthetic hand 1 to the initial position.

In particular, the return cable 341 controls a rotation of the phalanges 31 and 32 in the second direction. At the same time, the elastic means 63 return the movable elements 62 to the initial position, assisting said rotation in the second direction of the phalanges 31 and 32.

The underactuated prosthetic hand 1 and the prosthetic finger 3 according to the invention achieve important advantages.

In fact, it synergistically controls all fingers 3 and 3a with a geometrically and physically rational arrangement that achieves a gripping capacity and adaptation perfectly simulating a natural hand. In particular, the prosthetic hand 1 allows an extensive gripping capacity without complications from the point of view of use and control of said hand which in fact allows an automatic adaptation to the object to be grasped.

This aspect is achieved by having an underactuated prosthetic hand 1 having three dedicated single cable routings 5a and 5b, wherein the insertion of two guides 61 allows the division of the overall routing respectively into: thumb (routing master) controlled by the first control cable 5a; index and middle finger (routing 1) controlled by a second control cable 5b; and ring and small finger (routing 2) controlled by a different second cable 5b.

Another advantage is that the prosthetic finger 3 and thus the underactuated prosthetic hand 1 allow passive movement of the fingers 3 and/or 3a with the actuator 4 off thanks to the return block 34 and/or elastic means 63.

One important advantage is the use of multiple transmission blocks 6 which allows a high response rate of the underactuated prosthetic hand 1. In fact, when a finger 3 or 3a is blocked by an external obstacle, the cable portion 5b and/or 5a associated with it remains stationary while the remainder of said cable remains free to slide and continue closing the unblocked fingers 3 and/or 3a.

An important advantage lies in the fact that the underactuated prosthetic hand 1 allows the closure of fingers 3 and/or 3a to continue with a higher response rate and lower energy loss than a known hand. In fact, the particular kinematism of the underactuated prosthetic hand 1 is characterized by lower frictions and therefore by a faster response.

Another advantage is that it has two guides 61 each provided with a movable element 62 with a pair of pulleys 64 and 65 in series permitting a homogeneous distribution of the actuation force to be achieved.

A further advantage is that the prosthetic hand 1 is compact, highly elastic, adjustable, reliable and highly customizable depending on the anthropomorphic shape of each finger.

This aspect is accentuated by the particular fingers 3 and 3a. Each of them in fact has its own passive elastic recall system (the return block 34) independent and able to function as a return even when the fingers 3 and/or 3a are manually closed from the outside.

Variations may be made to the invention described herein without departing from the scope of the inventive concept defined in the claims. In said sphere all the details may be replaced with equivalent elements and the materials, shapes and dimensions may be as desired.

The invention claimed is:

1. An underactuated prosthetic hand comprising
a base body;
at least a pair of prosthetic fingers comprising a first prosthetic finger and a second prosthetic finger; each of said prosthetic fingers being hinged to said base body;
a first control cable;
an actuator adapted to move said first control cable;
and for each one of said pair of prosthetic fingers
   a second control cable having a first control end associated with said first prosthetic finger and a second control end associated with said second prosthetic finger; and
   a transmission block adapted to allow said first control cable to control said second control cable;
wherein said transmission block comprises
a guide integral with said base body and defining a sliding axis;
a movable element sliding along said guide; and
a first pulley for the sliding of said first control cable hinged to said movable element and
a second pulley for the sliding of said second control cable hinged to said movable element so that said actuator, when it moves said first control cable, brings about a translational movement of said movable element along said guide, causing a displacement of said second control cable and therefore of said prosthetic fingers; and
elastic means suitable to work in opposition to a translational movement of said movable element so that said translational movement of said movable element is performed in opposition to said elastic means, allowing said elastic means to command the return to the initial position of said movable element when said actuator is deactivated, so as to facilitate the return to the initial position of said main fingers; and
wherein said underactuated prosthetic hand comprises two of said at least one pair of prosthetic fingers; one said first control cable, two of said second control cable and two transmission blocks, each of which adapted to allow said first control cable to simultaneously control both said second control cables and thus both said pairs of prosthetic fingers.

2. The underactuated prosthetic hand according to claim 1, wherein said two transmission blocks comprise guides substantially parallel to each other.

3. The underactuated prosthetic hand according to claim 1, wherein each transmission block comprises two of said guide substantially parallel to each other; and wherein said movable element slides along said two guides.

4. The underactuated prosthetic hand according to claim 1, wherein each of said prosthetic fingers comprises a return block adapted to work in opposition to a rotation of said prosthetic finger controlled by said second control cable.

5. The underactuated prosthetic hand according to claim 1, comprising an additional finger adapted to work in opposition to said prosthetic fingers; and wherein said first control cable is adapted to control said additional finger.

6. The underactuated prosthetic hand according to claim 5, wherein said additional finger comprises one said return block adapted to work in opposition to a rotation of said additional finger controlled by said first control cable.

7. The underactuated prosthetic hand according to claim 1, wherein said pulleys define rotation axes substantially parallel to each other and substantially perpendicular to said sliding axis.

8. The underactuated prosthetic hand according to claim 1, which is mono-actuated and comprises a single actuator.

9. The underactuated prosthetic hand according to claim 1, wherein said elastic means comprise at least one compression coil spring extending coaxially with said sliding axis.

10. The underactuated prosthetic hand according to claim 9, wherein each transmission block comprises two of said guide substantially parallel to each other; and wherein said movable element slides along said two guides.

11. The underactuated prosthetic hand according to claim 10, wherein each of said prosthetic fingers comprises a return block adapted to work in opposition to a rotation of said prosthetic finger controlled by said second control cable.

* * * * *